United States Patent
Ehman et al.

(10) Patent No.: US 7,034,534 B2
(45) Date of Patent: Apr. 25, 2006

(54) PRESSURE ACTIVATED DRIVER FOR MAGNETIC RESONANCE ELASTOGRAPHY

(75) Inventors: Richard L. Ehman, Rochester, MN (US); Phillip J. Rossman, Rochester, MN (US); Thomas C. Hulshizer, Utica, MN (US); M. Alex Dresner, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/860,174

(22) Filed: Jun. 3, 2004

(65) Prior Publication Data

US 2005/0270029 A1   Dec. 8, 2005

(51) Int. Cl.
*G01V 3/00* (2006.01)

(52) U.S. Cl. ...................... 324/318; 324/319
(58) Field of Classification Search ............... 324/318, 324/309, 307, 300, 322, 319; 600/438

See application file for complete search history.

(56) References Cited

U.S. PATENT DOCUMENTS

| | | | |
|---|---|---|---|
| 5,032,793 A | 7/1991 | Yamaoto et al. | |
| 5,277,184 A | 1/1994 | Messana | |
| 5,313,945 A | 5/1994 | Friedlander | |
| 5,592,085 A | 1/1997 | Ehman | |
| 5,606,971 A | 3/1997 | Sarvazyan | |
| 5,810,731 A * | 9/1998 | Sarvazyan et al. | 600/438 |
| 5,877,732 A | 3/1999 | Ziarati | |
| 5,952,828 A | 9/1999 | Rossman et al. | |
| 5,977,770 A | 11/1999 | Ehman | |
| 6,037,774 A | 3/2000 | Felmlee et al. | |
| 6,486,669 B1 | 11/2002 | Sinkus et al. | |
| 2003/0210811 A1 * | 11/2003 | Dubowsky et al. | 382/128 |

* cited by examiner

*Primary Examiner*—Brij B. Shrivastav
(74) *Attorney, Agent, or Firm*—Quarles & Brady LLP

(57) ABSTRACT

A driver for use in applying an oscillating stress to a subject undergoing a magnetic resonance elastography (MRE) examination includes a passive actuator located in the bore of the magnet and in contact with the subject. A remotely located acoustic driver produces acoustic energy in response to an applied current and this energy is coupled therethrough a flexible tube to the passive actuator. A movable element in the passive actuator vibrates in response to this acoustic energy.

12 Claims, 3 Drawing Sheets

PRESSURE ACTIVATED DRIVER FOR MAGNETIC RESONANCE ELASTOGRAPHY

STATEMENT REGARDING FEDERALLY SPONSORED RESEARCH

This invention was made with government support under Grant No. CA91959 & EB001982 awarded by the National Institute of Health. The United States Government has certain rights in this invention.

BACKGROUND OF THE INVENTION

The field of the invention is nuclear magnetic resonance imaging methods and systems. More particularly, the invention relates to devices for implementing MR elastography.

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging ("MRI") systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient a physician can feel differences in the compliance of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the above imaging modalities. Tumors (e.g. of the liver) that are undetected by existing imaging modalities and cannot be reached for palpation through the patient's skin and musculature, are often detected by surgeons by direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

It has been found that MR imaging can be enhanced when an oscillating stress is applied to the object being imaged in a method called MR elastography (MRE). The method requires that the oscillating stress produce shear waves that propagate through the organ, or tissues to be imaged. These shear waves alter the phase of the NMR signals, and from this the mechanical properties of the subject can be determined. In many applications, the production of shear waves in the tissues is merely a matter of physically vibrating the surface of the subject with an electromechanical device such as that disclosed in above-cited U.S. Pat. No. 5,592,085. For example, shear waves may be produced in the breast and prostate by direct contact with the oscillatory device. Also, with organs like the liver, the oscillatory force can be directly applied by means of an applicator that is inserted into the organ.

A number of driver devices have been developed to produce the oscillatory force needed to practice MRE. As disclosed in U.S. Pat. Nos. 5,977,770; 5,952,828; 6,037,774 and 6,486,669 these typically include a coil of wire through which an oscillating current flows.

This coil is oriented in the polarizing field of the MRI system such that it interacts with the polarizing field to produce an oscillating force. This force may be conveyed to the subject being imaged by any number of different mechanical arrangements. Such MRE drivers can produce large forces over large displacement, but they are constrained by the need to keep the coil properly aligned with respect to the polarizing magnetic field. In addition, the current flowing in the driver coil produces a magnetic field which can alter the magnetic fields during the magnetic resonance pulse sequence resulting in undesirable image artifacts.

Another approach is to employ piezoelectric drivers as disclosed in U.S. Pat. Nos. 5,606,971 and 5,810,731. Such drivers do not produce troublesome disturbances in the scanner magnetic fields when operated, but they are limited in the forces they can produce, particularly at larger displacements. Piezoelectric drivers can also be oriented in any direction since they are not dependent on the polarizing magnetic field direction for proper operation.

SUMMARY OF THE INVENTION

The present invention is an MRE driver which can produce large forces over large displacements without interfering with the MRI system and which may be oriented in any direction on the subject. More specifically, the MRE driver includes an acoustic driver located remotely from the MRI system which is operable in response to an applied electrical current to oscillate; a passive actuator is positioned on a subject in the MRI system and has a housing which defines a chamber and a flexible membrane which covers an opening into the chamber; and a tube is acoustically coupled at one end to the acoustic driver and is acoustically coupled at its other end to the chamber in the passive actuator. Oscillations of the acoustic driver are coupled through the tube to the passive actuator chamber to cause the flexible membrane to oscillate. The membrane rests against the subject of interest to apply a corresponding oscillatory force to the subject during the MRE examination.

A general object of the invention is to produce large oscillatory forces to a subject during an MRE scan without interfering with the operation of the MRI system. The oscillatory force is produced by the acoustic driver which is located remotely from the MRI system magnetic fields. Thus, any magnetic fields that are produced by the acoustic driver will not interfere with scanner operation. The passive actuator can have a variety of shapes and sizes depending on the clinical application, and it can be oriented in any direction on the subject.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

The physical properties of tissue are measured using MR elastography by applying a stress (e.g. tension, pressure, or shear) and observing the resulting strain (e.g. elongation, compression, rotation). By measuring the resulting strain, elastic properties of the tissue such as Young's modulus, Poisson's ratio, the shear modulus, and the bulk modulus, can be calculated. By applying the stress in all three dimensions and measuring the resulting strain, the elastic properties of the tissue can be completely defined.

By observing the rate at which the strain decreases as a function of distance from the stress producing source, the attenuation of the strain wave can be estimated. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

Figure 1:
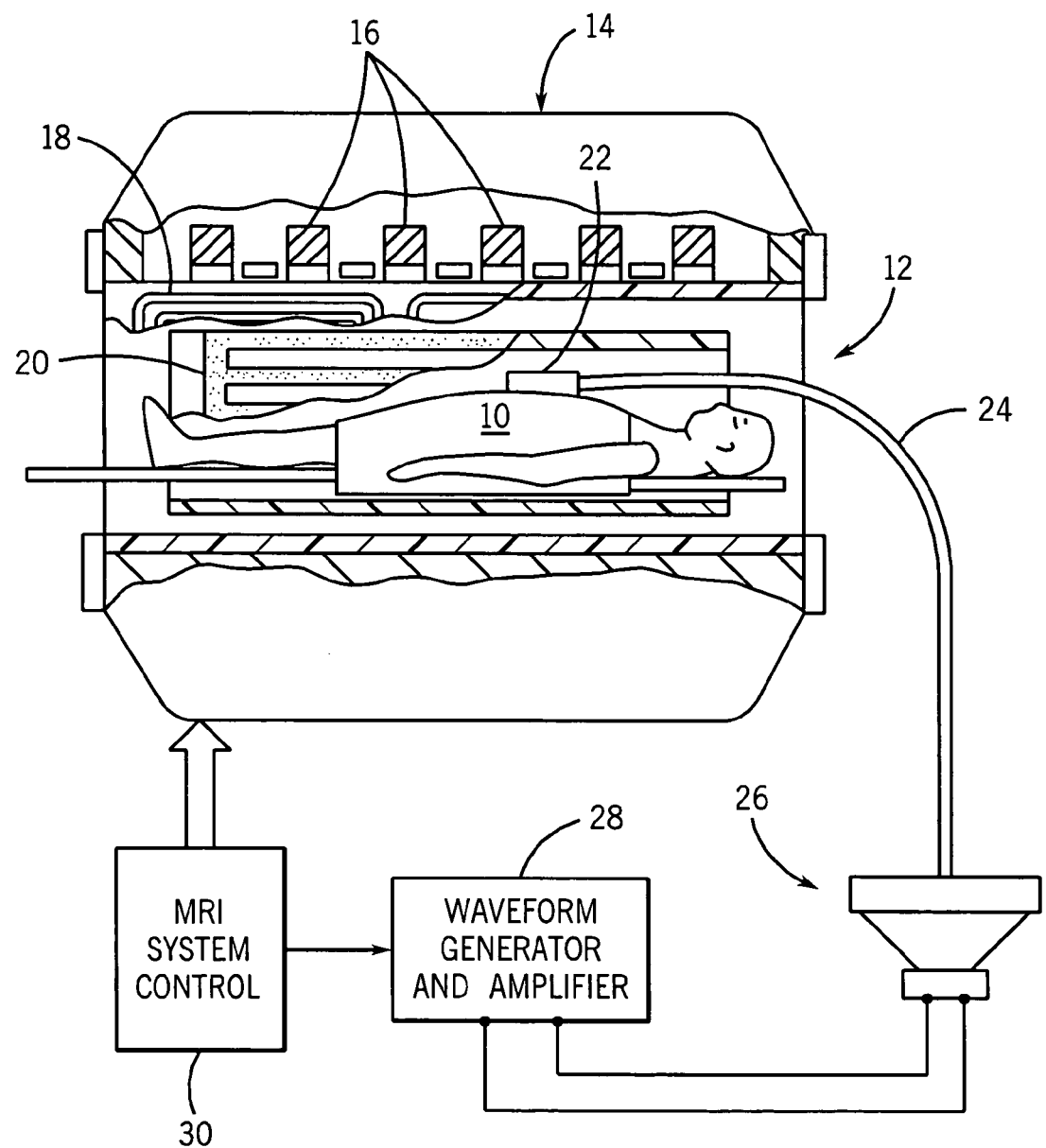
FIG. 1 is a pictorial representation of an MRI system which employs the preferred embodiment of the present invention.

The present invention is employed in a system such as that described in the above-cited U.S. Pat. No. 5,592,085 which provides a means for measuring the strain in gyromagnetic materials such as tissues using NMR methods and apparatus. Referring particularly to FIG. 1, a subject to be examined 10 is placed in the bore 12 of an MRI system magnet 14 and is subjected to magnetic fields produced by a polarizing coil 16, gradient coils 18 and an RF coil 20 during the acquisition of NMR data from the region of interest in the subject 10. The homogeneity of these magnetic fields are important and any objects placed in the bore 12 must be carefully constructed of materials that will not perturb them.

The present invention is an MRE driver which may be placed on the subject 10 and energized to produce an oscillating stress. It includes a passive actuator 22 which is positioned over the region of interest in the subject 10 and is connected by means of a tube 24 to a remotely located acoustic driver assembly 26. The acoustic driver assembly 26 is remote from the bore 12 of the magnet 14 in the sense that it is away from the strong magnet fields produced by the magnet 14 where its operation is not impeded by those fields, and where its operation will not perturb the MRI system magnetic fields. The acoustic driver assembly 26 is electrically driven by a waveform generator and amplifier 28, which in turn is controlled by the pulse sequencer in the MRI system control 30. The MRI system control 30 directs the MRI system to perform an MRE scan by driving the RF coil 20, and the gradient coils 18 in the magnet assembly 14 to perform a series of pulse sequences, while enabling the waveform generator 28 at the proper moment during each pulse sequence to apply an oscillatory stress to the subject 10 as described in the above-cited U.S. Pat. No. 5,592,085.

Figure 2:
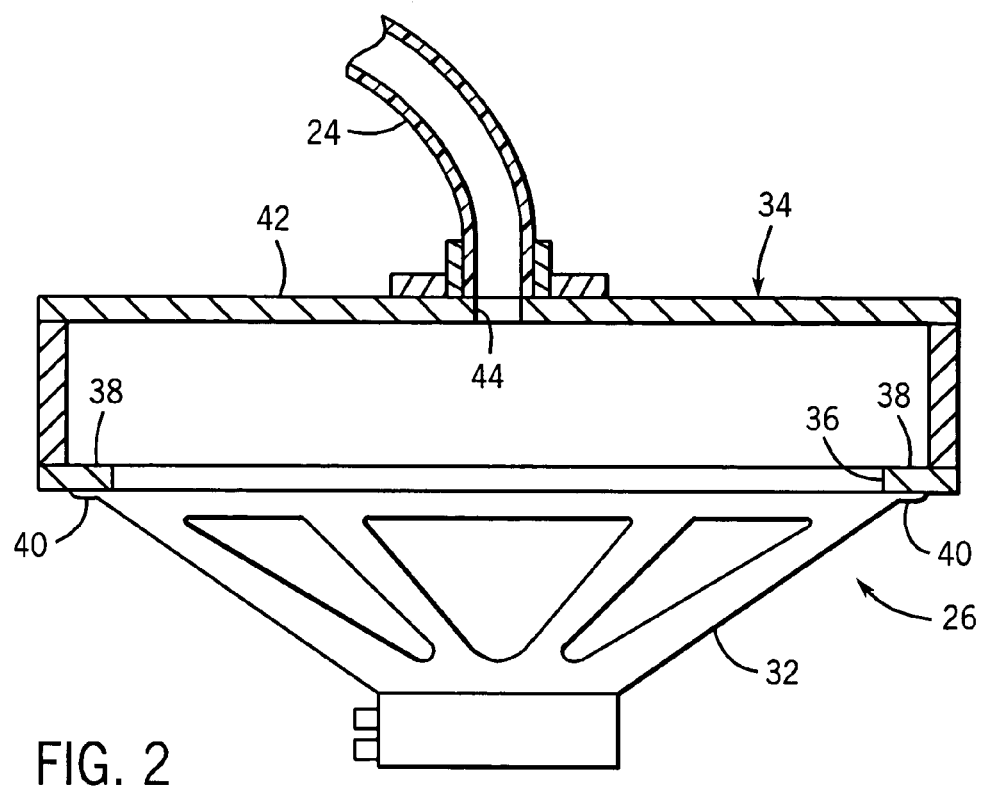
FIG. 2 is a pictorial view of the acoustic driver used in the system of FIG. 1.

Referring particularly to FIG. 2, the acoustic driver assembly 26 is comprised of a loudspeaker 32 mounted on one side of a thin enclosure 34. The loudspeaker 32 is a 15 inch speaker manufactured by Resonant Engineering and sold as Model SE15. It has a resonant frequency of 30 Hz and can handle 1000 watts peak power or 600 watts rms. The enclosure 34 is constructed of a rigid material such as polycarbonate, and in the preferred embodiment it is a rectangular enclosure having a dimension of 18"×18"×1.5". A large opening 36 is formed in one wall 38 of the enclosure 34 and the flange 40 on the loudspeaker 32 fastens to this wall such that the speaker 32 directs acoustic energy directly into the enclosure 34.

One end of the tube 24 connects to the opposite wall 42 of enclosure 34 and is acoustically coupled to its interior by an output opening 44. As a result, the acoustic energy produced by the loudspeaker 32 is directly coupled to one end of the tube 24 through the thin enclosure 34.

The tube 24 is made of a material which is flexible, but which is not elastic. The flexibility enables it to be fed along a winding path between the subject in the magnet and the remote site of the acoustic driver assembly 26. In the preferred embodiment the tube 24 is 20 feet long and has an inside diameter of 1.0 inches. It is made of a clear vinyl material sold under the trademark "TYGON" and has a wall thickness of approximately one-eighth inch. It is non-elastic such that it does not stretch in response to the variations in air pressure caused by the acoustic energy it conveys. As a result, the acoustic energy is efficiently conveyed from the driver assembly 26 to the passive actuator 22.

Figure 3:
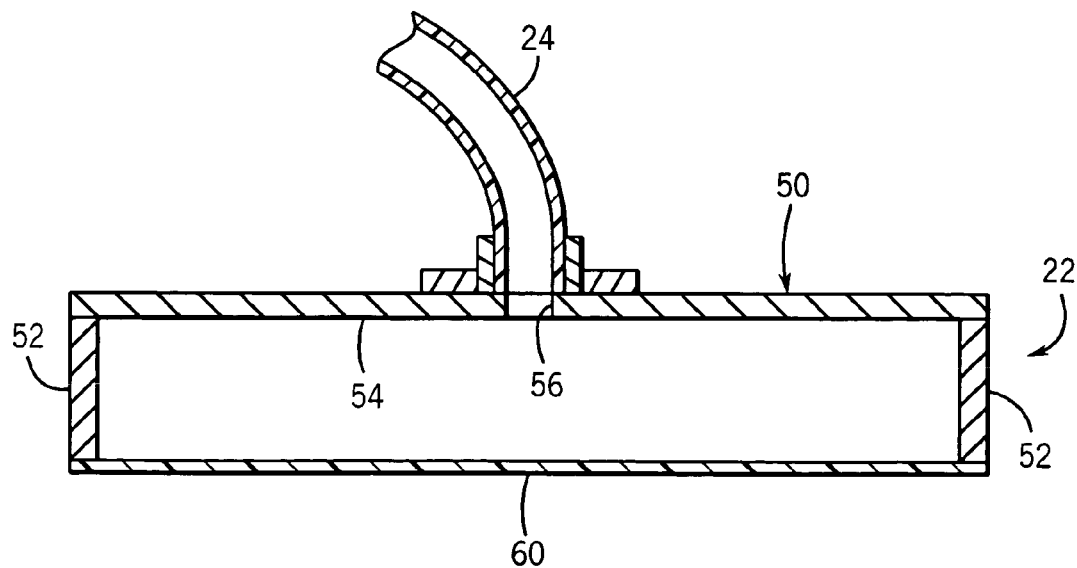
FIG. 3 is a view in cross-section of the passive actuator which forms part of the system of FIG. 1.

Referring particularly to FIG. 3, the passive actuator 22 is comprised of a cylindrical shaped enclosure 50 connected to the end of the tube 24. The size of this enclosure 50 will vary depending on the particular clinical application, and applicants have embodiments ranging from 1 to 10 inches in diameter. The enclosure is formed by a rigid, cylindrical outer wall 52 and a rigid circular end wall 54 that connects to one end of the outer wall 52. An input hole 56 is formed in the outer wall 52 or end wall 54 to acoustically couple the tube 24 to the interior chamber of the enclosure 50. The Rigid walls 52 and 54 are made of a polycarbonate or other non-ferous, non-electrically conducting material which is both rigid and relatively "invisible" to the magnetic fields produced in the bore 12 of the magnet 14.

Stretched across the other end of the cylindrical outer wall 52 is a flexible membrane 60. The membrane 60 can be made of a rubber or any sufficiently elastic material, but in the preferred embodiment it is a very thin sheet (10–20 micron thick) of a poly carbonate material. This flexible membrane 60 rests against the surface of the subject 10 and vibrates in response to the acoustic energy received through the tube 24. The variations apply an oscillating stress to the subject's skin which is conveyed into the region of interest. The space, including the interior of tube 24 and the interior of enclosures 34 and 50 is rigidly defined and completely enclosed. As a result, vibrations of the loudspeaker cone in the driver assembly 26 are efficiently conveyed acoustically to the flexible membrane 60 in the passive actuator 22.

Because the passive actuator 22 is constructed only of materials which will not perturb magnetic fields, and because it does not require the use of electric current to operate, it can be freely located anywhere within the bore 12 of the magnet 14. There is no need to align it in any particular direction to operate, and it can be placed very close to the region of interest without producing image artifacts.

The present invention can produce stress levels that are comparable to those produced by electromagnetically operated drivers. In the preferred embodiment a Crown model CH1 amplifier is employed and it delivers 450 to 900 watts into a 4 to 8 ohm loudspeaker load. Unlike many electromagnetically operated drivers, the preferred embodiment of the present invention applies oscillating stress in the longitudinal direction. The longitudinal stress is converted by tissue to a transverse stress which produces shear waves in the tissues of interest.

Figure 4:
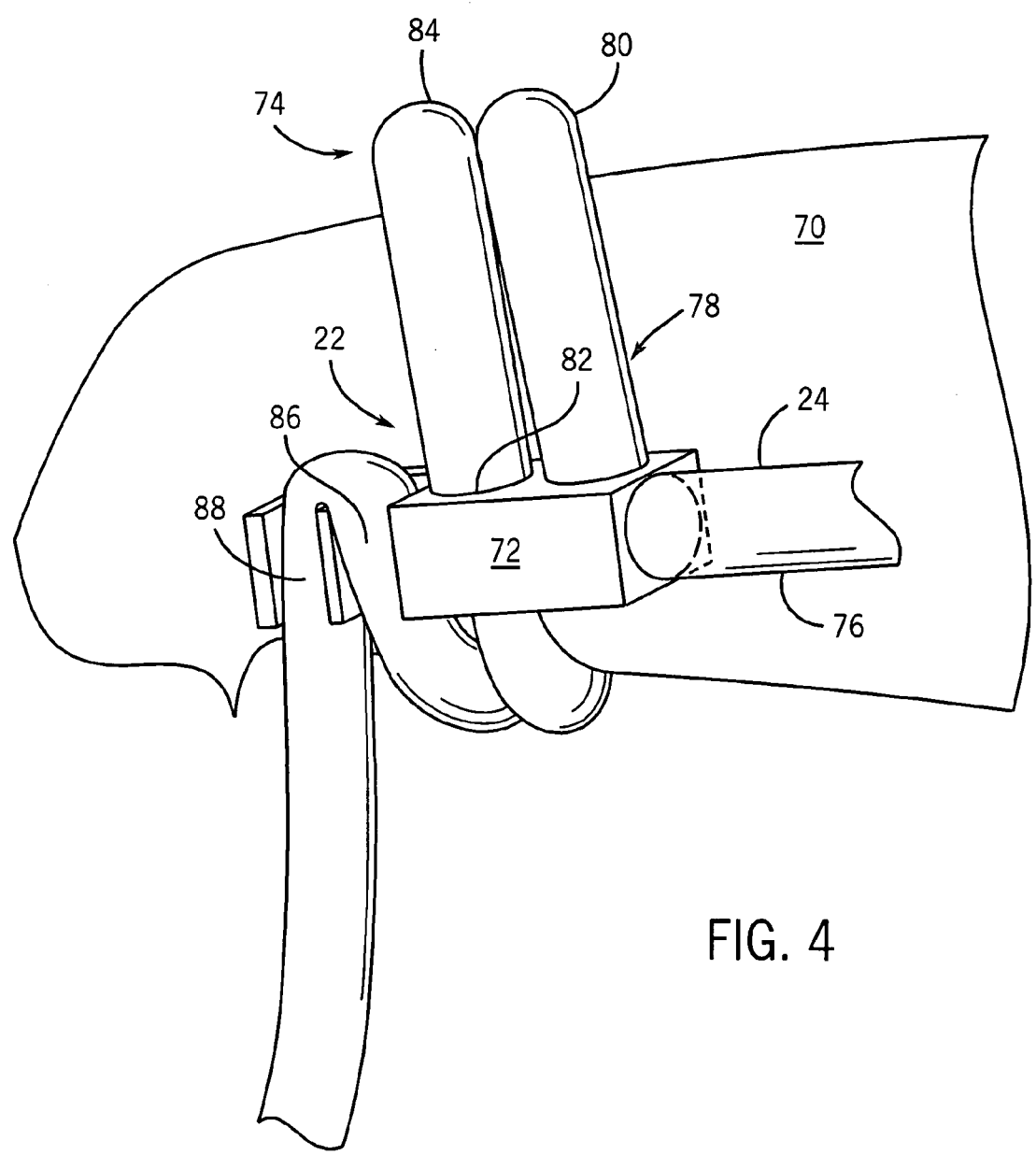
FIG. 4 is a pictorial view of an alternative embodiment of the passive actuator which forms part of the system of FIG. 1.

Referring particularly to FIG. 4, an alternative embodiment of the passive actuator 22 may be used when imaging an appendage such as the arm or leg. In the clinical application shown the passive actuator 22 is attached to the leg 70 of a patient. The passive actuator includes a manifold 72 which connects to the tube 24 and couples the acoustic energy therein to an elastic hose 74. The tube 24 connects to an opening 76 at one end of the manifold 72 and one end of the elastic hose 74 connects to an output opening 78 in the top of the manifold. The elastic hose 74 wraps around the subject's leg 70 in a first loop 80, feeds through a channel 82 formed in the manifold 72, and wraps around the leg 70 again to form a second loop 84. The distal end of the elastic hose 74 wraps through two slots 86 and 88 formed in the manifold 72 to pinch off the end. The elastic hose 74 can be fed through the channel 82 and slots 86 and 88 to adjust the size of the loops 80 and 84 to fit snuggly around the subject's leg 70 at different locations, or to fit around the subject's arm.

The elastic hose 74 forms an air tight band around the subject's appendage which applies an oscillating constrictive force to the appendage in response to the acoustic energy received through the flexible tube 24. The elastic hose 74 is made of silicone tubing which expands and contracts in diameter in response to the applied acoustic energy. Expansion of the hose diameter tightens or constricts around the subject's leg 70 and contraction of the diameter loosens the grip around the leg 70. This oscillating constrictive force applied around an appendage has been found to produce very good MRE images of structures in the appendage.

What is claimed is:

1. A driver for producing a stress on a subject while performing a magnetic resonance elastography scan in a magnetic resonance imaging (MRI) system, the combination comprising:
    an acoustic driver located remotely from the MRI system and being operable to produce acoustic energy;
    a passive actuator positioned in the MRI system and having an enclosure with an opening therein and a flexible membrane stretched across the opening; and
    a tube which acoustically couples the acoustic driver to the passive actuator such that the flexible membrane vibrates in response to the acoustic energy produced by the remotely located acoustic driver.

2. The driver as recited in claim 1 in which the acoustic driver includes a loudspeaker mounted over an opening in an enclosure, and the tube acoustically couples to the interior of the enclosure through a second opening therein.

3. The driver as recited in claim 1 in which a second opening is formed in the passive actuator enclosure and the tube acoustically couples to the interior of said enclosure through said second opening.

4. The driver as recited in claim 1 in which the tube is flexible.

5. The driver as recited in claim 1 in which the passive actuator and the tube are made of materials which do not substantially perturb magnetic fields produced by the MRI system.

6. The driver as recited in claim 5 in which the passive actuator is made of polycarbonate materials.

7. A driver for use with a magnetic resonance imaging (MRI) system, the combination comprising:
    an acoustic driver being operable in response to an applied electrical current to produce acoustic energy;
    a passive actuator constructed of materials which do not perturb magnetic fields produced by the MRI system, the passive actuator having an element which moves in response to acoustic energy applied to one side of the element; and
    a tube having one end connected to the acoustic driver and a second end connected to the passive actuator, the tube being operable to couple acoustic energy from the acoustic driver to said one side of the moving element in said passive actuator and having a length sufficient to position the passive actuator in a bore of the MRI system and to position the acoustic driver outside the bore of the MRI system.

8. The driver as recited in claim 7 in which the moving element is an elastic tube which expands and contracts in diameter in response to acoustic energy coupled to its interior.

9. The driver as recited in claim 8 in which the elastic tube is configured to extend substantially around an appendage of a subject placed in the MRI system.

10. The driver as recited in claim 7 in which the acoustic driver includes a loudspeaker mounted over an opening in an enclosure, and the tube acoustically couples to the interior of the enclosure through a second opening therein.

11. The driver as recited in claim 7 in which the passive actuator includes an enclosure with an opening therein and the moving element is a flexible membrane extending across said opening.

12. The driver as recited in claim 11 in which a second opening is formed in the passive actuator enclosure and the tube acoustically couples to the interior of said enclosure through said second opening.

* * * * *